(12) United States Patent
Wu et al.

(10) Patent No.: US 7,639,360 B2
(45) Date of Patent: Dec. 29, 2009

(54) EXAMINING DEVICE AND EXAMINING METHOD

(75) Inventors: Chun-Wei Wu, Chiayi (TW);
Cheng-Chung Hu, Taoyuan County (TW); Chiu-Jung Huang, Changhua County (TW); Chao-Song Chang, Taipei (TW); Huan-Ting Li, Changhua County (TW)

(73) Assignee: Chunghwa Picture Tubes, Ltd., Taoyuan (TW)

( * ) Notice: Subject to any disclaimer, the term of this patent is extended or adjusted under 35 U.S.C. 154(b) by 0 days.

(21) Appl. No.: 12/203,927

(22) Filed: Sep. 4, 2008

(65) Prior Publication Data

US 2009/0168065 A1    Jul. 2, 2009

(30) Foreign Application Priority Data

Dec. 31, 2007    (TW) .............................. 96151571 A

(51) Int. Cl.
*G01J 4/00* (2006.01)
*G02F 1/13* (2006.01)

(52) U.S. Cl. .................. 356/364; 356/369; 349/117; 349/136; 428/1.1

(58) Field of Classification Search ......... 356/364–369, 356/432–440, 499; 349/117, 87, 104, 136; 428/1.1, 131, 138; 353/38, 99, 122; 209/524, 209/579
See application file for complete search history.

(56) References Cited

U.S. PATENT DOCUMENTS

| 4,636,786 | A  | * | 1/1987  | Haertling ..................... 345/84 |
| 5,141,110 | A  | * | 8/1992  | Trischan et al. ............. 209/524 |
| 5,659,411 | A  | * | 8/1997  | Nito et al. .................... 349/117 |
| 6,042,237 | A  | * | 3/2000  | De Vaan et al. ............... 353/38 |
| 6,177,153 | B1 | * | 1/2001  | Uchiyama et al. ............ 428/1.1 |
| 6,633,358 | B1 | * | 10/2003 | Kwok et al. ................. 349/136 |
| 2008/0116928 | A1 | * | 5/2008  | Kim et al. .................... 324/770 |
| 2008/0304079 | A1 | * | 12/2008 | Schluchter et al. .......... 356/499 |

FOREIGN PATENT DOCUMENTS

TW    440737    6/2001

* cited by examiner

*Primary Examiner*—Sang Nguyen
(74) *Attorney, Agent, or Firm*—Jianq Chyun IP Office

(57) ABSTRACT

An examining device adapted to examining a transmittance of a display panel is provided. The examining device includes a light source, a first polarizer, a photodetector, a second polarizer, at least one first reflector and at least one second reflector. The light source and the photodetector are respectively disposed on both sides of the display panel. The second polarizer is disposed between the display panel and the photodetector. The first reflector is disposed between the display panel and the second polarizer. The second reflector is disposed between the display panel and the first polarizer. Light emitting from the light source successively passes via the first polarizer, the display panel, the first reflector, the display panel, the second reflector, the display panel, the second polarizer and then emits into the photodetector.

7 Claims, 2 Drawing Sheets

EXAMINING DEVICE AND EXAMINING METHOD

CROSS-REFERENCE TO RELATED APPLICATION

This application claims the priority benefit of Taiwan application serial no. 96151571, filed on Dec. 31, 2007. The entirety of the above-mentioned patent application is hereby incorporated by reference herein and made a part of specification.

BACKGROUND OF THE INVENTION

1. Field of the Invention

The present invention is directed to an examining device and examining method, and more particularly, to an examining device and examining method used for examining a retardation value and a transmittance of a display panel.

2. Description of Related Art

Nowadays, multimedia technology has been well developed, which is benefited from the development of semiconductor devices and display apparatuses. As for displays, liquid crystal displays (LCDs) having advantages, such as high image display quality, good space utilization, low power consumption and radiation-free have gradually become the mainstream products of the market.

Taking a thin film transistor LCD (TFT-LCD) module for example, it is mainly consisted of an LCD panel and a backlight module. The LCD panel is consisted of a TFT array substrate, a color filter substrate (C/F substrate) and a liquid crystal layer disposed therebetween. The backlight module is used for providing the plane light source for the LCD panel so that the LCD module can achieve its desired display effects.

Usually, when a display panel is produced, the retardation value thereof is fixed. There is a certain relationship existing between the retardation value and the transmittance of the display panel, however, since a loss would occur when light emitting from the light source passes through the display panel, the transmittance obtained therefrom is lower than the actual transmittance of the display panel. For example, the transmittance of the display panel can be obtained through performing a laser light passing through the display panel and then dividing an original light intensity of the laser light by the light intensity of the laser light passing through the display panel. Ideally, when the transmittance is given, the retardation value can be inferred. However, the glass substrate, liquid crystal, polarizers, analyzers and pixel electrodes are possible to absorb or reflect the laser light so that the light intensity of the laser light is decayed. Thus, the retardation value obtained by the way of dividing the original light intensity of the laser light by the light intensity of the laser light passing through the display panel is not correct.

In other words, the retardation value obtained by such way can not correctly represent the actual retardation value of the display panel. Therefore, a measuring method of rotation polarizers is developed, for example, the one disclosed in Taiwan Patent No. TW00440737. However, such method requires a complicated system to control the rotation of the polarizers. The precision level of such measuring method is determined by how precisely the rotation of the palarizers is controlled.

SUMMARY OF THE INVENTION

The present invention is directed to an examining device adapted to examining a transmittance of a display panel.

The present invention is further directed to an examining method applying the examining device in examining a transmittance and a retardation value of a display panel.

The present invention is directed to an examining device adapted to examining a transmittance of a display panel. The examining device includes a light source, a first polarizer, a photodetector, a second polarizer, at least one first reflector and at least one second reflector. The light source is disposed on one side of the display panel, and the display panel is located on a light path of the light source. The first polarizer is disposed between the display panel and the light source and located on the light path of the light source. The photodetector is disposed on the light path of the light source. The photodetector and the first polarizer are respectively located on both sides of the display panel. The second polarizer is disposed between the display panel and the photodetector and located on the light path of the light source. The first reflector is disposed between the display panel and the second polarizer. The second reflector is disposed between the display panel and the first polarizer. The quantity of the first reflectors is equal to that of the second reflectors. The light emitting from the light source successively passes via the first polarizer, the display panel, the first reflector, the display panel, the second reflector, the display panel, and the second polarizer and then emits into the photodetector.

In one embodiment of the present invention, the light source is a laser light source.

In one embodiment of the present invention, the photodetector is a charge coupled device (CCD) photodetector.

In one embodiment of the present invention, the photodetector is a complementary metal-oxide semiconductor (CMOS) photodetector.

In one embodiment of the present invention, the photodetector is a photodiode photodetector.

In one embodiment of the present invention, the display panel is a twisted nematic (TN) display panel.

The present invention is directed to an examining method adapted to examining a retardation value and a transmittance of a display panel. The detection method includes the following steps. An examining device as described in the above is provided, and the display panel is disposed between the first and the second reflectors. The display panel is emitted by utilizing the light source, and a light intensity $T(1)$ and a light intensity $T(N)$ are measured with the photodetector, wherein the light intensity $T(1)$ represents the light intensity measured from the light emitting from the light source and passing just once through the display panel, while the light intensity $T(N)$ represents the light intensity measured by the light emitting from the light source and passing for N times through the display panel via the first and the second reflectors. A curve of given transmittances and the retardation values is provided. A loss of the light emitting from the light source and passing through the display panel is L, and $L=[A-T(1)]/A$. Herein, A represents the light intensity measured by the light emitting from the light source and passing just once through the first polarizer and the second polarizer without passing through the display panel. The transmittance Tr of the display panel is:

$$Tr = \frac{T(1)(1-L^{N-1})}{T(N)}.$$

Then, the transmittance and the retardation value of the display panel are obtained by the curve of transmittances and retardation values.

Based on the above, the present invention measures the light intensity of the light emitting from the light source and passing once or for many times through the display panel and obtains the retardation value by the curve of given transmittances and the retardation values. Therefore, in comparison with the prior art, the method of the present invention is quicker. Furthermore, the examining device of the present invention can be also applied in production lines so as to perform real-time examining.

In order to make the aforementioned and other objects, features and advantages of the present invention more comprehensible, preferred embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF EMBODIMENTS

Figure 1:
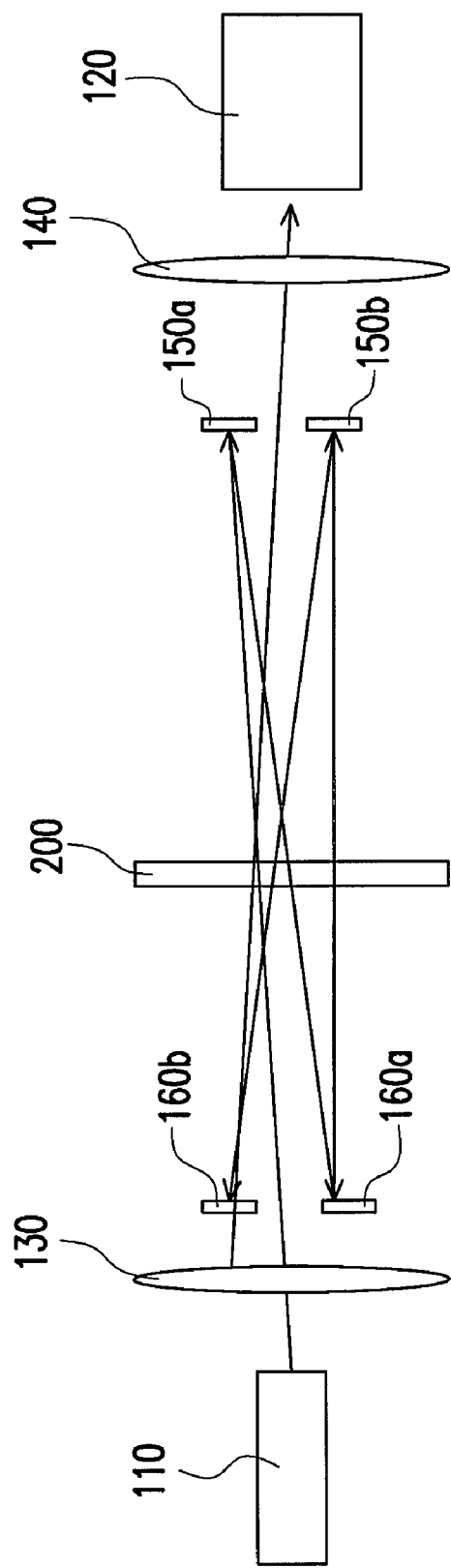
FIG. 1 is a schematic view of an examining device according to one embodiment of the present invention.

FIG. 1 is a schematic view of an examining device according to one embodiment of the present invention. The examining device of the present invention is adapted to examining a transmittance of a display panel 200. The examining device includes a light source 110, a photodetector 120, a first polarizer 130, a second polarizer 140, first reflectors 150a, 150b and second reflectors 160a, 160b. The light source 110 and the photodetector 120 are respectively disposed on both sides of the display panel 200, and the display panel 200 is located on a light path of the light source 110. The first polarizer 130 is disposed between the display panel 200 and the light source 110 and located on the light path of the light source 110. The second reflectors 160a, 160b are disposed between the display panel 200 and the first polarizer 130. The second polarizer 140 is disposed between the display panel 200 and the photodetector 120 and located on the light path of the light source 110. The first reflectors 150a, 150b are disposed between the display panel 200 and the second polarizer 140.

The light emitting from the light source 110 successively passes via the first polarizer 130, the display panel 200, the first reflector 150a, the display panel 200, the second reflector 160a, the display panel 200, the first reflector 150b, the display panel 200, the second reflector 160b, the display panel 200 and the second polarizer 140 and then emits into the photodetector 120. In the present embodiment, the quantity of the first reflectors 150a, 150b is equal to that of the second reflectors 160a, 160b, that is, two reflectors. However, the present invention can merely have the first reflector 150a and the second reflector 160b. In addition, the light source 110 can be a laser light source, infrared light source, ultraviolet light source, visual light source, or light sources with other wavelengths. The photodetector 120 can be a complementary metal-oxide semiconductor (CMOS) photodetector, a charge coupled device (CCD) photodetector, photodiode photodetector or other types of photodetectors. Moreover, the display panel 200 is, for example, a twisted nematic (TN) display panel.

Hereinafter, the method of examining the transmittance and the retardation value of the display panel 200 by utilizing the examining device will be described.

Continually referring to FIG. 1, first, the display panel 200 is disposed between the first reflectors 150a, 150b and the second reflectors 160a, 160b. Then, the display panel 200 is emitted by utilizing the light source 110. A light intensity T(1) and a light intensity T(5) are measured with the photodetector 120. The light intensity T(1) represents the light intensity measured from the light emitting from the light source 110 and passing just once through the display panel 200, while the light intensity T(5) represents the light intensity measured from the light emitting from the light source 110 and passing for 5 times through the display panel 200 via the first reflectors 150a, 150b and the second reflectors 160a, 160b. The light intensity T(1) and the light intensity T(5) are substituted into the following formulas:

$$L = [A - T(1)]/A \quad (1);$$

$$Tr = \frac{T(1)(1 - L^{N-1})}{T(N)}. \quad (2)$$

Referring to formula (1), A represents the light intensity measured from the light emitting from the light source 110 and only passing through the first polarizer 130 and the second polarizer 140 without passing through the display panel, that is, the influences of the first polarizer 130 and the second polarizer 140 upon the light intensity are measured. T(N) presents the light emitting from the light source 100 and passing for N times through the display panel 200. In the present embodiment, N is 5. L represents a loss of the light emitting from the light source 110 and passing through the display panel 200.

Referring to the formula (2), Tr represents the transmittance of the display panel 200.

Figure 2:
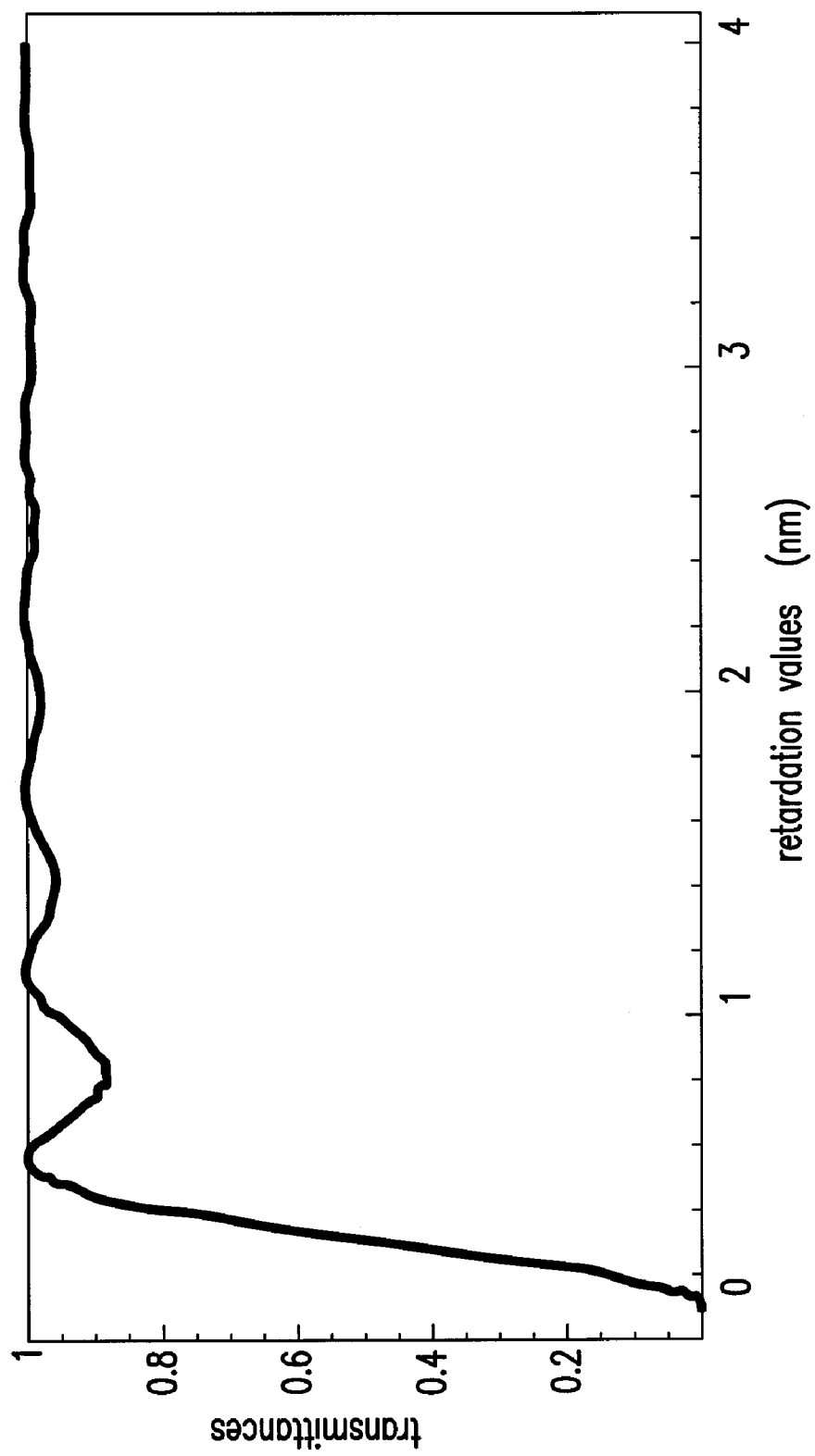
FIG. 2 is a curve diagram of given transmittances and retardation values.

FIG. 2 is a curve diagram of given transmittances and retardation values. Referring to FIG. 2, Tr obtained from the formula (2) is substituted into FIG. 2 so that a retardation value can be obtained. Herein, such examining method will be described by an example.

First, A is measured as 791 micro-watts. A represents a light intensity measured from the light emitting from the light source and passing just once through the first polarizer 130 and the second polarizer 140. Meanwhile, light intensity T(1) is 147 micro-watts. The light intensity T(1) represents the light emitting from the light source 110 and passing just once through the display panel 200. Then, light intensity T(5) is 0.1894 micro-watts. The light intensity T(5) represents the light intensity measured from the light emitting from the light source 110 and passing for 5 times through the display panel 200. When the subject values are substituted into the formula (2), a transmittance (Tr) of 0.923482 can be obtained. Then, such value is substituted into FIG. 2 so that a retardation value of 374 nano-meters (nm) can be obtained. It should be noted that the more times the light emitting from the light source 110 passes through the display panel 200, the more accurate the measuring method would be. The present embodiment is not intended to be limited to adopting a method of searching in a table for obtaining a retardation value, and FIG. 2 can also be converted to a formula for obtaining a retardation value.

In comparison with the prior art, only the light source 110, the photodetector 120, the first reflectors 150a, 150b and the second reflectors 160a, 160b are required for the present invention to obtain the transmittance and the retardation value of the display panel 200. Thus, the present invention does not need any expensive polarizer drivers and controlling instruments. In other words, the cost required for present invention is lower than the prior art. In addition, the present invention can measure the transmittance and retardation value of the display panel 200 to be examined quicker than the prior art.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. An examining device adapted to examining a transmittance of a display panel, comprising:
    a light source disposed on one side of the display panel and the display panel is located on a light path of the light source;
    a first polarizer disposed between the display panel and the light source, which is located on the light path of the light source;
    a photodetector disposed on the light path of the light source, wherein the photodetector and the first polarizer are respectively located on both sides of the display panel;
    a second polarizer disposed between the display panel and the photodetector, which is located on the light path of the light source;
    at least one first reflector disposed between the display panel and the second polarizer; and
    at least one second reflector disposed between the display panel and the first polarizer, and the quantity of the first reflector being equal to that of the second reflector, wherein light emitting from the light source successively passes via the first polarizer, the display panel, the first reflector, the display panel, the second reflector, the display panel and the second polarizer and then emits into the photodetector.

2. The examining device as claimed in claim 1, wherein the light source is a laser light source.

3. The examining device as claimed in claim 1, wherein the photodetector is a charge coupled device (CCD) photodetector.

4. The examining device as claimed in claim 1, wherein the photodetector is a complementary metal-oxide semiconductor (CMOS) photodetector.

5. The examining device as claimed in claim 1, wherein the photodetector is a photodiode photodetector.

6. The examining device as claimed in claim 1, wherein the display panel is a twisted nematic (TN) display panel.

7. An examining method adapted to examining a retardation value and a transmittance of a display panel, comprising:
    providing the examining device of claim 1, and disposing the display panel between the first reflector and the second reflector;
    emitting the display panel by utilizing the light source and measuring a light light intensity T(1) and a light intensity T(N) with the photodetector, wherein the light intensity T(1) represents the light intensity measured from the light emitting from the light source and passing just once through the display panel, while the light intensity T(N) represents the light intensity measured by the light emitting from the light source and passing for N times through the display panel via the first and the second reflectors; and
    providing a curve of given transmittances and the retardation values, wherein a loss of the light emitting from the light source and passing through the display panel is L, and L=[A−T(1)]/A, where A represents the light intensity measured from the light emitting from the light source and passing just once through the first polarizer and the second polarizer, and the transmittance Tr of the display panel is:

$$Tr = \frac{T(1)(1-L^{N-1})}{T(N)};$$

and
    obtaining the retardation value of the display panel from the curve of transmittances and retardation values.

* * * * *